(12) United States Patent
Tran

(10) Patent No.: US 12,201,755 B2
(45) Date of Patent: Jan. 21, 2025

(54) MODULAR CONTAMINATE CAPTURE AND STERILIZATION APPARATUS AND METHOD

(71) Applicant: Khanh Ngoc Tran, Austin, TX (US)

(72) Inventor: Khanh Ngoc Tran, Austin, TX (US)

(73) Assignee: Khanh Ngoc Tran, Austin, TX (US)

( * ) Notice: Subject to any disclaimer, the term of this patent is extended or adjusted under 35 U.S.C. 154(b) by 419 days.

(21) Appl. No.: 17/725,957

(22) Filed: Apr. 21, 2022

(65) Prior Publication Data

US 2022/0241452 A1 Aug. 4, 2022

Related U.S. Application Data

(62) Division of application No. 17/096,518, filed on Nov. 12, 2020, now Pat. No. 11,344,649.

(51) Int. Cl.
*A61L 9/20* (2006.01)
*B01D 53/86* (2006.01)

(52) U.S. Cl.
CPC ............ *A61L 9/20* (2013.01); *B01D 53/8675* (2013.01); *A61L 2209/111* (2013.01); *A61L 2209/14* (2013.01); *B01D 2257/106* (2013.01)

(58) Field of Classification Search
None
See application file for complete search history.

(56) References Cited

U.S. PATENT DOCUMENTS

| | | | |
|---|---|---|---|
| 2006/0283786 A1* | 12/2006 | Harbers | B01J 19/123 210/85 |
| 2019/0091738 A1* | 3/2019 | Chen | B60H 1/00742 |
| 2019/0240370 A1* | 8/2019 | Benedek | A61L 9/205 |
| 2020/0075972 A1* | 3/2020 | Jorgenson | A01M 1/2094 |

* cited by examiner

*Primary Examiner* — Jelitza M Perez
(74) *Attorney, Agent, or Firm* — K&L Gates LLP

(57) ABSTRACT

An apparatus and method are provided for capturing and sterilizing contaminants, such as viruses and the like. Air containing the contaminants is drawn into the apparatus that comprises a housing having a customized number and arrangement of dissimilar treatment chambers to remove a particular contaminate targeted for removal. The treatment chambers are selected from a group of pre manufactured, self-contained chambers that are singularly or in combination inserted into the housing and within an air flow path created by a fan. The group of treatment chambers include a UV chamber, a temperature chamber and an ozone converter chamber. The customized arrangement of treatment chambers are each placed in the air flow path and programmed to provide customized sterilization of any type of contaminate while persons are present in the space being treated.

14 Claims, 5 Drawing Sheets

MODULAR CONTAMINATE CAPTURE AND STERILIZATION APPARATUS AND METHOD

CROSS-REFERENCE TO RELATED APPLICATIONS

The present application is a divisional of and claims priority to pending U.S. patent application Ser. No. 17/095,518, filed Nov. 12, 2020, titled MODULAR CONTAMINATE CAPTURE AND STERILIZATION APPARATUS AND METHOD, the entire contents of which are hereby incorporated by reference herein and relied upon.

BACKGROUND

1. Field of the Invention

Example embodiments in general relate to an apparatus and system to capture and treat or sterilize airborne contaminants. In particular the apparatus and system captures and kills viruses, insects, microorganisms, pollution or other contaminants in the air using a self-contained and customized number and arrangement of treatment chambers, each of which can be independently programmed to change, in a closed loop setting, treatment intensity and duration as well as the volume, direction and duration of an air flow through each chamber while people are present in the space being treated.

2. Description of Related Art

Indoor air often contains contaminants that are harmful to the health and safety of its occupants. For example, air can be contaminated with pollution such as dust, formaldehyde, benzene, xylene, and other harmful gases that can cause respiratory diseases. Air can also be contaminated with bacteria, insects, microorganisms or odors that are not only noxious but harmful to people in general. Air can be contaminated with viruses that can cause illness in humans. For example, COVID-19 infected people have a wide range of symptoms from mild to severe and even death.

Traditional methods of disinfection or sterilization of contaminated air include the use of chemicals. While partially effective, the impact of chemical treatment may cause its own problems. Introducing caustic chemicals is not only dangerous but is only partially effective and may negatively contribute to problems of unwanted odors. Other sterilization methods include the introduction of heat to treat certain microorganisms and bacteria. Large heaters placed in an open room has proven effective in treating, for example, bed bugs in rooms. However, heat must be passed throughout the room, temporarily preventing occupants in the room during treatment. Also, to make the room habitable, the significant amount of heat applied to the room proves costly to remove.

A more recent treatment of contaminated air can include ultraviolet (UV) radiation. A UV lamp is typically placed in the middle of a room. However, due to the harmful effects of the high UV intensity needed to kill viruses, people must be evacuated from the room before and during activation of the UV lamp. Moreover, UV radiation will create ozone ($O_3$) into the room. Ozone introduced throughout a large space such as a room or building is difficult and expensive to thereafter gather, remove and/or convert back to habitable oxygen ($O_2$) levels. Whether treatment involves chemicals, heat or UV radiation, the treatment itself often proves harmful to anyone present during the treatment, or afterwards. The presence of the treatment agent in large spaces is difficult and expensive to thereafter remove to a level acceptable to human habitation.

It would be beneficial to sterilize all types of contaminated air, especially air containing viruses such as the COVID-19 virus. It would also be beneficial to sterilize the space while people are present in the space during treatment. Sterilization should occur in a way that will not emit noxious or harmful air into the treated space. It would be further beneficial to customize sterilization to the particular contaminate present, and to programmably control the amount of sterilization applied to the air in order to more effectively and efficiently rid the particular contaminate present, without undue and harmful overtreatment—all the while people are present during treatment.

SUMMARY

In accordance with at least one example of the disclosure, an apparatus is provided that can capture and sterilize contaminated air within any size space, whether a room, a building, or outdoors. The apparatus is portable and includes a housing with removable wheel so it can be oriented into various positions and readily placed in any size space. The housing includes a fan that can draw in contaminated air into the apparatus to sterilize the contaminated air while people are present in the space during treatment. The apparatus comprises modular, self-contained treatment chambers. The apparatus can therefore be configured with one or more of the self-contained treatment chambers so it is customized depending on the type of contaminate being treated.

In accordance with another example of the disclosure, the contaminate capture and sterilization apparatus can be customized to include a single treatment chamber, such as a UV chamber. The UV chamber can be arranged in the housing and downstream of an air flow path created by the fan. As noted herein, downstream connotes air flow that results from an upstream air flow formed by the fan or a chamber closer to the fan. The UV chamber can include a UV lamp that is programmably controlled with instructions stored in memory and executed upon by a processor having an output that is connected to the UV lamp. If desired, the apparatus can be further customized to include two treatment chambers. The first treatment chamber can be a UV chamber, and the second chamber can be a temperature chamber. The temperature chamber is arranged within the housing in a different slot than the UV chamber, and downstream of the air flow path within the UV chamber. The temperature chamber can include a heating element and a cooling element that are each programmably controlled by the processor and instructions stored in the memory.

If further desired, the apparatus can be customized to include three treatment chambers, the third chamber can be an ozone converter chamber arranged within the housing and downstream of the air flow path within the temperature chamber. Conversely, the ozone converter chamber can be arranged downstream of the UV chamber, and the apparatus can include, or not include, the intermediate temperature chamber. The ozone chamber can include a catalyst element that is programmably controlled to convert ozone to oxygen. Depending on the amount of ozone created by the UV lamp, the ozone chamber may or may not be needed. If the amount of ozone created is below a predetermined threshold, an ozone chamber will not be needed.

In accordance with another example of the disclosure, the contaminate capture and sterilization apparatus can include one or more sensors arranged in each self-contained chamber. Output from the UV lamp can be sensed by a UV sensor also arranged in the UV chamber. The UV sensor output is coupled to the processor, which then sends a command to the UV lamp depending on the instructions stored in the memory and on the output from the UV sensor. The same applies to the temperature chamber.

The temperature chamber can include a self-contained heating chamber and a self-contained cooling chamber, and can also include at least one temperature sensor. The temperature sensor, also arranged in the temperature chamber, can determine output from the heater and cooler. The temperature sensor output is coupled to the processor and, depending on the stored instructions and output from the temperature sensor, the processor commands the heater and/or cooler to apply additional heating and/or cooling to the air flow path within the temperature chamber.

In accordance with at least one other example of the disclosure, each treatment chamber can further include a moveable baffle. The moveable baffle within each chamber can change the volume and direction of the air flow path within that respective chamber. Each treatment chamber can also include a moveable damper. The damper is moved independently in each chamber to re-direct air flow from the respective chamber and back into that chamber to maintain air flow (and thus contaminated air) within that chamber for a time duration necessary to treat that contaminated air. Each treatment chamber has its own baffle and damper, and the baffle and damper are contained solely within its respective chamber and are independently moved relative to each other and relative to other chamber's baffles and dampers to control the volume, direction, and treatment exposure duration of the contaminated air drawn into the housing from the space into which the apparatus is placed.

The memory can store treatment profile data. The profile data preferably comprises a desired treatment amount and duration. The desired treatment amount and duration is unique to a particular contaminate which a user wishes to eliminate. For example, the desired treatment amount and duration applicable to the UV chamber comprises the amount of output intensity from the UV lamps as well as the duration at which the UV lamps irradiate the air flowing past the lamps. The desired duration not only applies to the amount of time the UV lamps emit radiation, but also the amount by which the UV chamber baffles are mostly closed to keep air in the UV chamber and the UV chamber dampers are mostly opened to keep air recirculating back into the UV chamber and across the UV lamps. All of the other chambers, depending on whether they will be selected for use and therefore inserted into the housing, also have a profile data of a desired treatment amount and duration. For example, the desired treatment amount and duration applicable to a temperature chamber comprises the heating and cooling element output intensity and duration, as well as the duration at which the temperature chamber baffles and dampers are mostly closed and mostly opened.

The closed loop system therefore not only applies to programming the processor control outputs with various chamber treatment amounts and treatment durations based on previously stored treatment profiles, but also performs the closed loop control using sensors coupled to the processor or controller. The sensors detect an amount of treatment being applied in respective chambers, and the sensors forward that amount to the processor. The processor, armed with the treatment profile data stored in memory, can then send control signals to the various devices (emitters, heating elements, cooling elements, ozone catalysts, baffles and dampers) to change the treatment amounts and durations to conform to the appropriate treatment profile and the sensor output.

In accordance with yet another example of the disclosure, a method is provided for capturing and sterilizing contaminated air. The method includes inserting at least one self-contained treatment chamber comprising a UV chamber, a temperature chamber or an ozone converter chamber, or a combination thereof, into a housing. Once customized with the appropriate treatment chamber, or chambers, an air flow path of contaminated air is drawn into the housing during operation. The drawn air is passed through the at least one treatment chamber previously inserted into the housing. The volume, direction and thus duration of the air flow path through the at least one treatment chamber is programmably and independently changed via the processor output. Also, the amount, or intensity, of treatment of the contaminated air within the air flow path can be programmably and independently changed via the processor instructions and the sensor readings.

BRIEF DESCRIPTION OF THE DRAWINGS

For a detailed description of various examples, reference will now be made to the accompanying drawings in which.

DETAILED DESCRIPTION

This description is generally directed to an apparatus and method to sterilize a physical space. The apparatus is customizable with modular self-contained treatment chambers to sterilize the physical space depending on the type of contaminate in that space. If the contaminate is bacterial and not viral, or is chemical and not dust, an appropriate treatment chamber or chambers can be arranged into a housing of the apparatus. If the type of contaminate being treated changes, the previous chamber or chambers can be removed from the housing and a different chamber or chambers can be inserted. In addition, depending on the most efficient process for sterilization, the sequence of chambers can be modified relative to the air flow path. For example, a temperature chamber can be placed downstream of the air flow path within a UV chamber. Alternatively, the UV chamber can be placed downstream of the air flow path within the temperature chamber. Depending on the most effective and efficient sterilization mechanism, the order of different treatment chambers can be changed, as well as which treatment chamber (or chambers) is to be used.

This description is also generally directed to utilizing a processor and memory to execute upon stored treatment intensities and treatment time durations, and provide the same to the appropriate treatment chamber. A closed loop feedback can be used to sense treatments provided to the corresponding chamber and, along with the stored treatment intensities and stored time durations, the processor can forward control signals to the appropriate chambers. For example, if the sensed treatment temperature within the temperature chamber is too low for proper treatment at that time duration, then a control signal is sent from the processor to increase intensity or duration depending on the appropriate treatment temperature and duration stored in memory.

Figure 1:
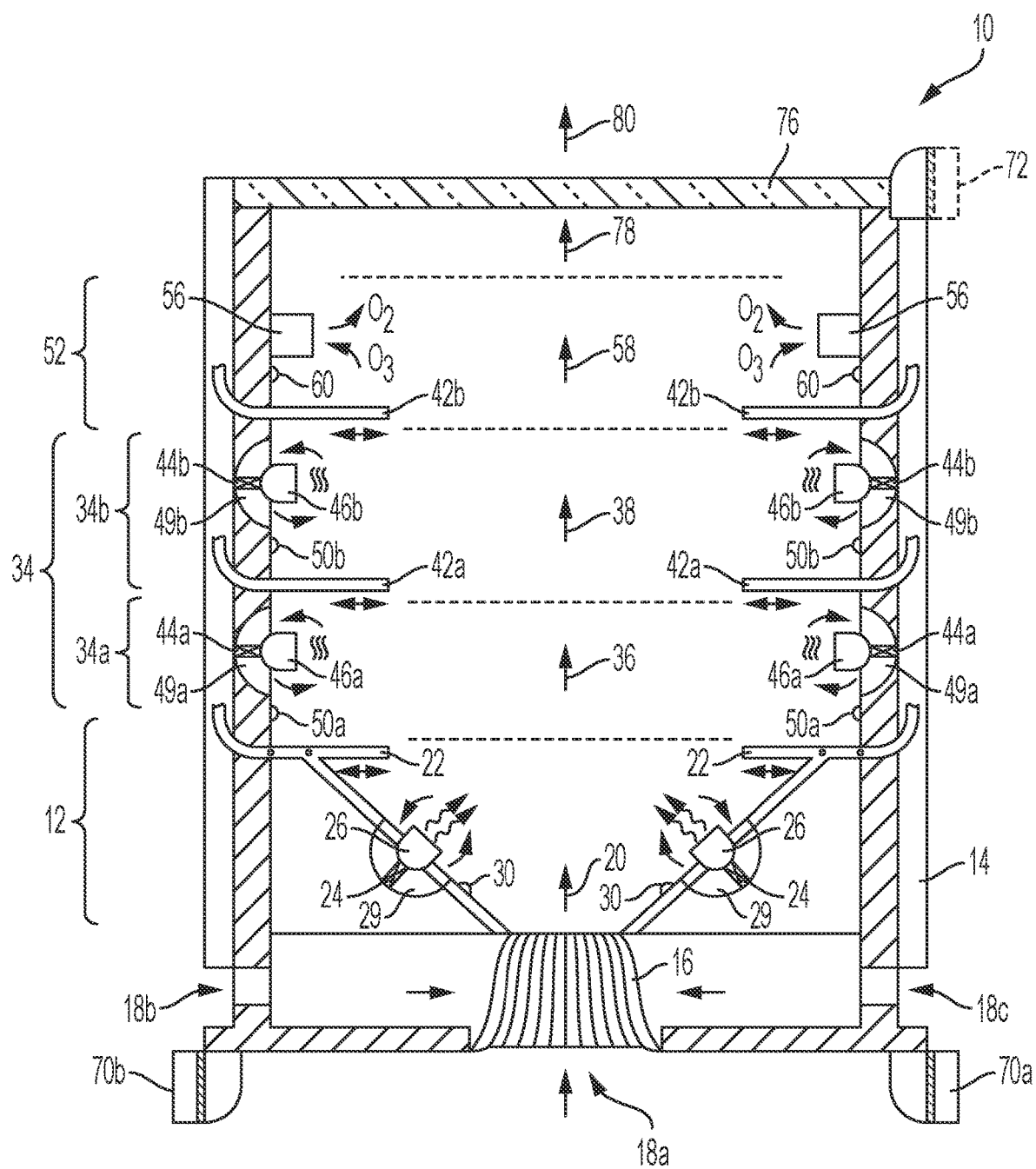
FIG. 1 is a side partial cross-sectional and plan view of a contaminate capture and sterilization apparatus in accordance with various examples.

Referring to the drawings, FIG. 1 shows an example of an apparatus 10 for capturing and sterilizing contaminated air. The contaminate can be a virus, such as COVID-19 virus. To effectively treat (i.e., kill) a virus, apparatus 10 can include a UV chamber 12 placed into a housing 14. The UV chamber 12 can be placed downstream of an air flow path created by fan 16. Fan 16 can be placed near the bottom of housing 14 to draw in contaminated air from, for example five sides. The five sides comprise an opening 18a in the bottom of the housing and four openings 18b, 18c, 18d and 18e (two openings 18d and 18e are not shown in the partial cross sectional view of FIG. 1) in the sides of the rectangular or square cube-shaped housing 14.

Rotation of fan around a vertical central axis pushes air upward and causes an air flow path 20 within UV chamber 12. The volume, direction and duration of air present within UV chamber 12 is controlled by a motorized moveable baffle 22 that, as shown, can move radially inward toward the vertical central axis of the housing 14 to constrict, reduce or eliminate air flow 20 from chamber 12. The greater the inward movement of baffle 22, the more air remains in chamber 12 and thus the longer the duration at which contaminated air is treated in the UV chamber 12.

In addition to having a moveable baffle 22, UV chamber 12 can also include a motorized, moveable damper 24. Damper 24 can move from a fully open to a fully closed positin to increase or decrease, respectively, the amount of air re-directed back into the UV chamber 12. By re-directing contaminated air back into the chamber 12, the amount and duration of air movement across the treatment element can be maintained. For example, by increasing the damper 24 opening, the greater the amount and duration of air flow 20 exists within chamber 12 and thus the greater amount of UV treatment per passing air unit can be achieved.

The damper 24 can be placed anywhere in the UV chamber 12, and is preferably near a sidewall surface of the chamber 12. More preferably, damper 24 should be placed adjacent to the treatment source, e.g., a UV lamp 26. A channel 29 can be formed around UV lamp 26, with the damper 24 configured within the channel 28. As the air flow 20 is drawn around UV lamp 26, possibly due to damper 24 being open and baffle 22 being at least partially closed, the effectiveness of UV radiation applied to the re-directed air flow is increased. An increase in UV treatment and duration can occur when the baffle 22 and damper 24 are programmably moved to their respective mostly closed and mostly open positions depending on the desired, previously stored intensity and duration values.

The UV intensity value at which viruses, such as COVID-19 can be effectively killed is with a wavelength range of 200-280 nanometers output from the UV lamp 26. The UV treatment duration is different depending on the amount of contaminant within the air flow path 20. However, to effectively kill 99.9% of most viruses at sufficient UV radiation intensity, the duration at which baffle 22 and damper 24 remain significantly closed and opened, is between 2 minutes to 15 minutes. The desired intensity and duration is stored in memory (volatile or non-volatile, static or dynamic, programmable or non-programmable) that can be fetched from memory by a processor as further denoted below.

To assist in achieving the desired intensity and duration, UV chamber 12 can include one or more UV sensors 30 preferably mounted on an inward facing sidewall surface of the UV chamber 12. According to one example, UV sensors 30 can be mounted on baffle 22 near UV lamps 26 if lamps 26 are also on the baffle 22. Similar to using multiple UV lamps 26, there can be two or more UV sensors 30 preferably placed within two or four centimeters of the UV lamps 26. Provided the UV lamps 26 face inward toward the air flow path 20, and that UV sensors 30 also face inward toward path 20 and the vertical central axis of housing 14, more effective UV radiation and accurate sensing can occur. The UV readings that are taken are sent to the processor, which reads what should be a target UV amount and makes the appropriate adjustment by sending a control signal to the UV lamp 26 to increase or decrease its UV output and/or to the baffle 22 and damper 24 to increase or decrease air flow duration within chamber 12.

In the example embodiment shown in FIG. 1, downstream of the air flow path 20 within UV chamber 12 is a temperature chamber 34. Temperature chamber 34 preferably comprises a heating chamber 34a immediately downstream of the air flow path 20 within UV chamber 12, and a cooling chamber 34b immediately downstream of the air flow path 36 within heating chamber 34a. The air flow path 38 within cooling chamber 34b is downstream of the air flow path 36 within heating chamber 34a.

Temperature chamber 34 can include its own baffles 42a, 42b contained with respective heating chamber 34a and cooling chamber 34b. Temperature chamber 34 also includes heater 46a and cooler 46b. Baffles 42a, 42b are similar in programmable operation to baffle 22, and heater/cooler 46a, 46b are similar in programmable operation to UV lamp 26. Temperature chamber 34 is self-contained, meaning each chamber sub chamber 34a, 34b has its own air flow volume and direction control, as well as its own treatment mechanisms and sensors. As will be further described below, each self-contained chamber need only be inserted into and removed from housing 14 in order to customize the overall treatment, and all electrical connections, functions and operations of treatment for each chamber are confined entirely and solely within that chamber.

Heating chamber 34a of temperature chamber 34 also includes a channel 49a with a damper 44a. The cooling chamber 34b of temperature chamber 34 also includes a channel 49b with a damper 44b. Damper 44a re-directs heated air flow back within chamber 34a, and damper 44b re-directs cooled air flow back within chamber 34b. Similar to damper 24 in UV chamber 12, dampers 44a and 44b can increase the duration at which air is maintained in the corresponding chambers 34a and 34b depending on the amount by which dampers 44*a* and 44*b* are opened. Dampers 44*a* and 44*b* are independently moved to ensure a different duration within chamber 34*a* than chamber 34*b*, if needed. Moreover, dampers 44*a*, 44*b* are preferably moved independent of damper 22 depending on the duration at which contaminates should be exposed to elevated temperatures relative to UV radiation.

Both the heating chamber 34*a* and the cooling chamber 34*b* can include heating sensors 50*a* and cooling sensors 50*b*, respectively. The heating and cooling sensors 50*a*, 50*b* are temperature sensors that sense the thermal energy or temperature in each chamber and provide that information to the processor. The processor can compare the sensed temperature to a target temperature stored in memory and can increase or decrease the output the heater 46*a* or cooler 46*b* commensurate with the difference. The target temperature and duration to effectively sterilize against a virus such as COVID-19 is around 56° C. (132.8° F.) at around 10000 units per 15 minutes. More preferably heat exceeding 92° C. would kill the COVID-19 virus is less time than 15 minutes. The temperature chamber 34, and especially the heating chamber 34*a* can be appropriately sized to accommodate a large enough volume of air, and the baffle 42*a* and damper 44*a* are maintained in a substantially closed and open position, respectively, for the rather lengthy duration before passing the treated air to the next downstream modular and self-contained chamber, such as an ozone converter chamber 52. Alternatively the fan speed of fan 16 can be reduced to lower the volume of air entering any of the chambers, including the temperature chamber 34, to allow sufficient treatment duration of 15 minutes or more per chamber.

The heater 46*a* and cooler 46*b* can be any device that converts electrical energy to thermal energy—thermoelectric or based on a compressor heating and cooling. The heater 46*a* is preferably placed adjacent to and downstream of the UV chamber 12 since the UV chamber in and of itself some thermal energy at the UV lamps 26. Thus, the air entering the heating chamber 34*a* will be somewhat preheated with this advantageous arrangement.

The temperature sensors 50*a*,50*b* can utilize a thermocouple contact or can use a non-contact infrared sensor technology. More preferably, sensors 50*a*,50*b* are resistance temperature detectors (RTDs). RTD temperature sensors 50*a*,50*b* are sensors whose resistance changes as its temperature change. As a passive, resistive-based, device, sensors 50*a*,50*b* are considerably less expensive than, for example, non-contact IR sensors. The sensors 50*a*,50*b* are preferably placed within several centimeters of the heater/cooler 46*a*,46*b* and preferably arranged on an inward facing sidewall surface.

If the UV lamp 26 produces wavelength emission below 242 nm, toxic ozone (03) will be produced in chamber 12. Depending on the quantities produced, inhaling ozone can cause shortness of breath, chest pain, wheezing and coughing. If ozone is too high, in some instances more serious symptoms can occur. The ozone converter chamber 52 preferably contains a catalyst element 56. Catalyst element 56 operates as a filter that is coupled to a power supply and to the processor to either remove the ozone ($O_3$) present in chamber 52 or convert ozone with oxygen (02).

If desired, the air flow path 58 in ozone converter chamber 52 can be controlled. Although not shown a baffle and a damper can be contained within chamber 52 to re direct and maintain the air flow 58 for a sufficient duration needed to convert ozone to oxygen. Also, an oxygen or ozone sensor 60 can be arranged on a sidewall of the chamber 52 to sense oxygen or ozone levels. The sensed level is sent to the processor, and depending on that level the processor sends a control signal to the catalyst element 56 to increase or decrease the oxygen level corresponding to a target oxygen level stored in memory.

Apparatus 10 may also include a filter 76 made of any media such as paper, felt, synthetic poly and fiberglass having a MERV rating needed to remove particles from the air flow path 78 down to less than 0.5 micron, HEPA type filter, for example. The sterilized air 80 is expelled from the housing 14 of the portable apparatus 10 either with or without a HEPA filter 76.

Coupled to housing 14 are legs 70*a*, 70*b*, 70*c*, 70*d* (legs 70*c* and 70*d* are not shown in the cross-sectional view of FIG. 1) that are detachably placed at each corner of the rectangular or square cube that is housing 14. Legs 70*a*-70*d* can include rollers to easily transport the portable apparatus 10 to the space being treated. Also, legs 70*a*-70*b* can be removed and secured at different positions, possibly along a sidewall of housing 14, as shown by reference numeral 72. If placed on its side, fan 16 would draw in contaminated air from a side opening 18*a* having a central axis parallel to the floor, and four other openings 18*b*-*e* having a central axis perpendicular to the floor.

Figure 2:
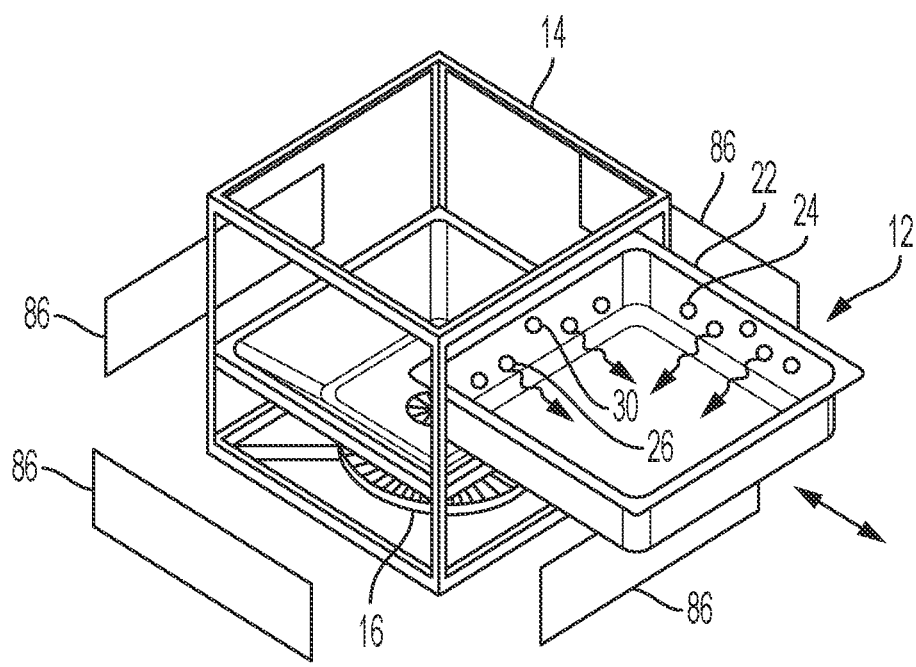
FIG. 2 is a top perspective view of the apparatus housing with a treatment chamber, such as a UV chamber, removeably configured within the housing in accordance with various examples.

FIG. 2 illustrates one module, the self-contained UV chamber 12, removeably arranged and coupled within housing 14 of apparatus 10. In this fashion, an apparatus 10 can be built by first manufacturing separately each module or chamber. Then, depending on which module will be used, an appropriate module is inserted into housing 14 at an appropriate position and in an appropriate order within the air flow path created by fan 16. Each module or chamber is entirely self-contained. The UV chamber 12 is shown arriving from the manufacturer self-contained and embodying all items for its full operation and functionality (i.e., the UV lamps 26, UV sensors 30, baffles 22 and dampers 24). Upon arrival, and if needed for the customized sterilization of apparatus 10, the self-contained module of chamber 12 is inserted into its proper location within the housing 14.

FIG. 2 also illustrates removeable panels 86 arranged around all four sides of housing 14. Panels 86 are removable around fan 16 for cleaning. Also, panels are removable above the fan 16 where each module or self-contained, previously manufactured, treatment chamber can be inserted and removed. As denoted in FIG. 3, panels 86 can include electrical connectors and slide-in grooves or ridges.

Figure 3:
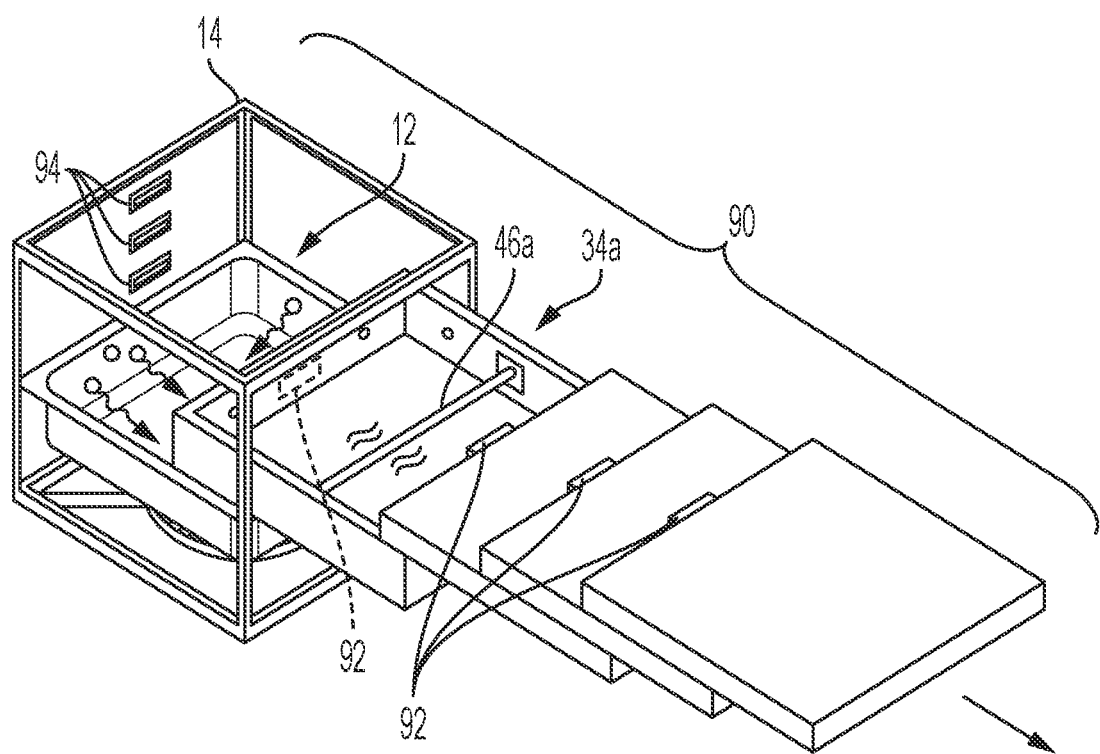
FIG. 3 is a top perspective view of the apparatus customized with one or more different treatment chambers removeably arranged within the housing depending on the particular contaminate being treated in accordance with various examples.

FIG. 3 illustrates a set of self-contained, previously manufactured modules or chambers 90. The set of chambers 90 can be, singularly or in combination, selectively and removeably configured and secured within housing 14. The set of chamber 90 can be secured by sliding each chamber into the appropriate position via slide-in grooves and utilizing any securement mechanism to hold the corresponding chamber in position within the housing 14. Moreover, on the backside of each chamber is an electrical connection 92 that mates with a corresponding electrical connection 94 arranged on a panel 86. Within panel 86 is an electrical line or bus that extends from electrical connection 94 to a control unit comprising a processor and memory, as shown in FIG. 4.

The number of chambers of the set of chambers 90 being inserted can vary. It may only be necessary to insert a temperature chamber 34, or a UV chamber 12, for example. Also, the order of chambers being inserted can vary. For example, the temperature chamber 34 can be inserted next to fan 16, or a UV chamber 12 can be inserted next to fan 16 with a temperature chamber 34 heat chamber 34*a* portion inserted downstream of the UV chamber 12 as shown.

Figure 4:
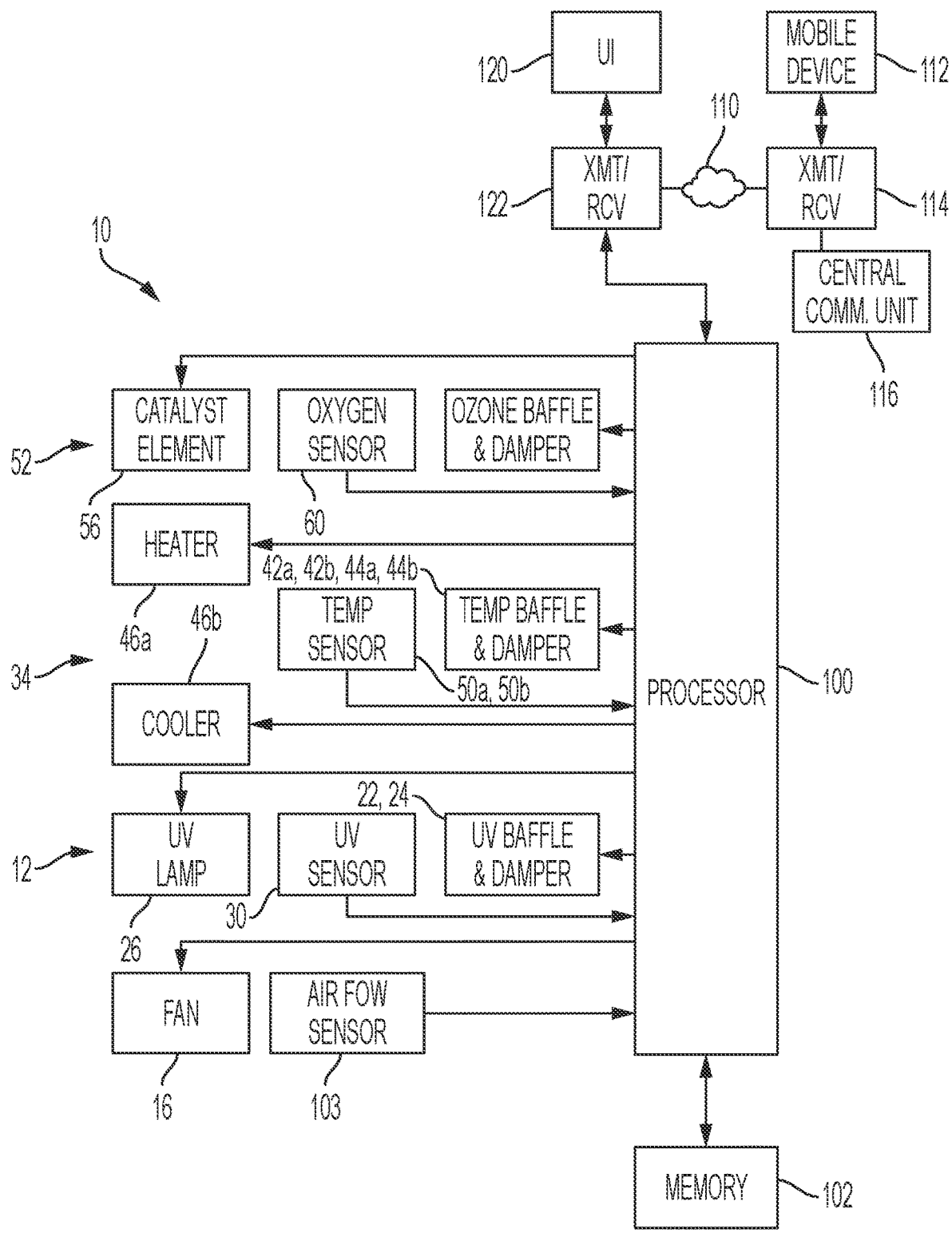
FIG. 4 is a block diagram of the functional relationship between components of the apparatus to programmably and independently control the intensity and duration of treatment and the volume, direction and duration of contaminated air being treated in each chamber in accordance with various examples.

FIG. 4 is a block diagram of the various components of apparatus 10, and remote communication thereto. Apparatus 10 includes an electrical supply system, such as AC mains to drive a power supply that conditions an appropriate electrical energy to its various components. Most of the components are pre-installed in the pre-manufactured, self-contained chambers 12, 34 and 52. For example, UV lamp 26, UV sensor 30 and UV baffle and damper 22, 24 are already embodied within the UV chamber 12. Heater 46a, cooler 46b, temperature sensor 50a, 50b and temperature baffle and damper 42a, 42b, 44a and 44b are already embodied within the temperature chamber 34. Catalyst element 56 and oxygen sensor 60 (as well as an ozone baffle and damper if utilized) are already embodied within the ozone chamber 52. As noted the various sensors 30, 50a, 50b and 60 can send a sensed intensity value to processor 100. Processor 100 operates as a control unit that, upon receipt of the sensed intensity value, sends back a control signal to UV lamp 26, heater 46a, cooler 46b and catalyst element 56 to modify its output depending on the sensed value and a target value stored in memory 102.

Processor 100 can also control the various UV, temperature, and ozone baffles and dampers. Depending on the air exposure duration needed (as stored in memory 102) and the sensed intensity, processor 100 sends a control signal to the various baffles and dampers to control the duration at which air is treated in each chamber. The target intensity and duration values can be updated in memory 102, and processor 100 can update its control signal output depending on any desired treatment recipe to sterilize any type of contaminate.

If needed, processor 100 can also control the speed of fan 16. One way to control the speed is to send a control signal to fan 16 depending on the stored fan target speed in memory 102. Another way to control fan 16 speed is to read the speed of air flow on an air flow sensor 103 and, based on the sensed air flow speed and a target air flow speed in memory 102, send a control signal to fan 16 to adjust the speed of fan 16 to obtain the target air flow speed.

The apparatus 10 may be utilized with and upon any telecommunications network 110 capable of transmitting data. Examples of suitable telecommunications networks in which apparatus 10 is configured includes global computer networks (e.g., Internet), wireless networks, cellular networks, satellite communications networks, cable communications networks (e.g., cable modem), local area networks (LAN), wide area networks (WAN), etc. Various protocols may be utilized by the electronic devices, such as a mobile device 112 communicating over a transmitter/receiver 114, communicating via HTTP, SMTP, FTP, WAP and wireless networks including CDMA, TDMA, 3/4/5G, Bluetooth and Zigbee, etc. A central communication unit 116 may be comprised of a server computer, cloud based computer, etc. A modem or other communication device may be required between each central communication unit 14 and the corresponding network 110, said modem can be encompassed within the transmitter/receiver 114.

Apparatus 10 may further comprise a user interface panel 120 in communication with processor 100 via a transmitter/receiver link 122. In lieu of or in addition to control of apparatus 10 via a server 116 or mobile device 112 linked over the network 119, a touch screen panel 120 can be mounted to apparatus 10. The LCD touch screen 120 is mounted and readily accessible to a user to allow the user to enter data directly into the apparatus 10, including target recipe data for memory 102.

Processor 100, in addition to its control function, can also log all failures occurring in the various chambers and/or the effectiveness of sterilization. If any component fails, or if the released air contains and undue amount of contaminants, processor 100 will report malfunction via, for example, a visual or audio monitor and log all failures during the lifetime of apparatus 10. The log is stored in memory 102 and can be harvested with a password consent for future product improvement and upgrades. Apparatus 10 can also include self-diagnostic hardware testing.

Figure 5:
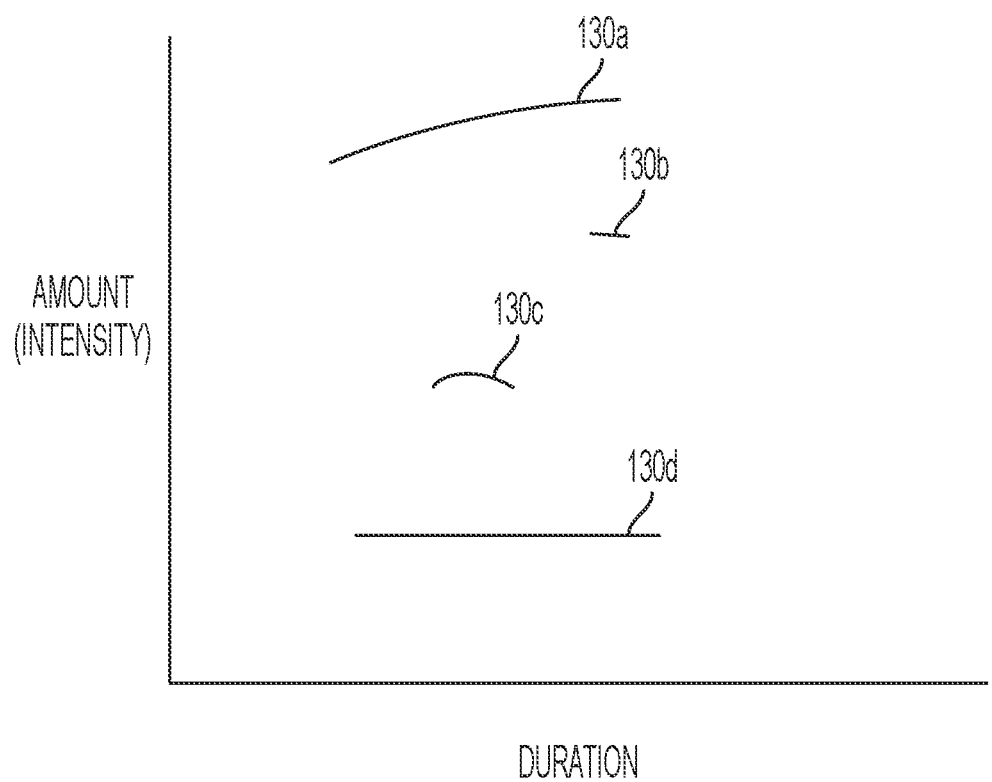
FIG. 5 is a graph of different treatment profile datum that can be stored in memory, each having a desired treatment amount and duration unique to sterilizing, in a closed loop setting, a particular contaminate targeted for treatment by the customizable apparatus.

FIG. 5 is a set of treatment profiles 130a, 130b, 130c, 130d, etc. of a desired treatment amount and duration of treatments for corresponding different contaminates targeted for sterilization. The profiles 130 can be stored in memory 102, and subsequently read by processor 100 in a closed loop control environment. For example, profile 130a may be used to eliminate COVID-19. The profile 130a for killing COVID-19 can be loaded from publically available resources over the central communication unit 116, or manually loaded by a user via the user interface 120 or mobile device 112. The profile 130a can correspond to the heating chamber 34a, for example, and can apply to the heating temperature amount and duration at which the contaminated air is exposed to the elevated temperature. Or, profile 130a can correspond to the UV chamber 12, for example, and can apply to the UV intensity amount (or wavelength) for the UV lamp output, and the duration at which contaminated air is exposed to the UV radiation. Other profiles 130b, 130c, 130d, etc. can correspond to other desired treatment amounts and durations unique to sterilizing other types of contaminates such as other viruses, microorganisms, pollution, insects, etc.

The treatment profile data of desired treatment amounts and durations are unique to different, corresponding, contaminates. To maintain those desired amounts and durations, a closed loop feedback mechanism is used. A sensor in a corresponding chamber can send the sensed treatment amount to the processor, that then reads the desired treatment amount from memory. If the sensed amount is different from the desired amount (for that treatment profile or regimen), then the processor sends a control signal to the corresponding chamber to increase or decrease the treatment amount. Also, the duration can be sensed by timing the duration at which a baffle is substantially closed and/or the fan is turned substantially off. If the baffle and fan is not maintained in their proper positions/operations for sufficient time, the processor will sense improper movement thereof and compare the timeout period to the desired treatment duration and, through the closed loop system, move the baffle or stop the fan for the appropriate, desired duration.

In the graph of FIG. 5, no scale or units need be given. Each profile 130 is indicative of a desired treatment amount that can be in temperature, ozone catalyst output, fan speed, and UV radiation, each with different units or scale. FIG. 5 is intended to show examples of relative differences between desired amounts and durations for different treatments applied to different chambers. The amounts can vary slightly, as can durations. For example, as noted above the wavelength range can extend from 200 to 280 nanometers, and the durations for UV treatment can extend between 2-15 minutes if the profile 130 is to kill COVID-19.

Figure 6:
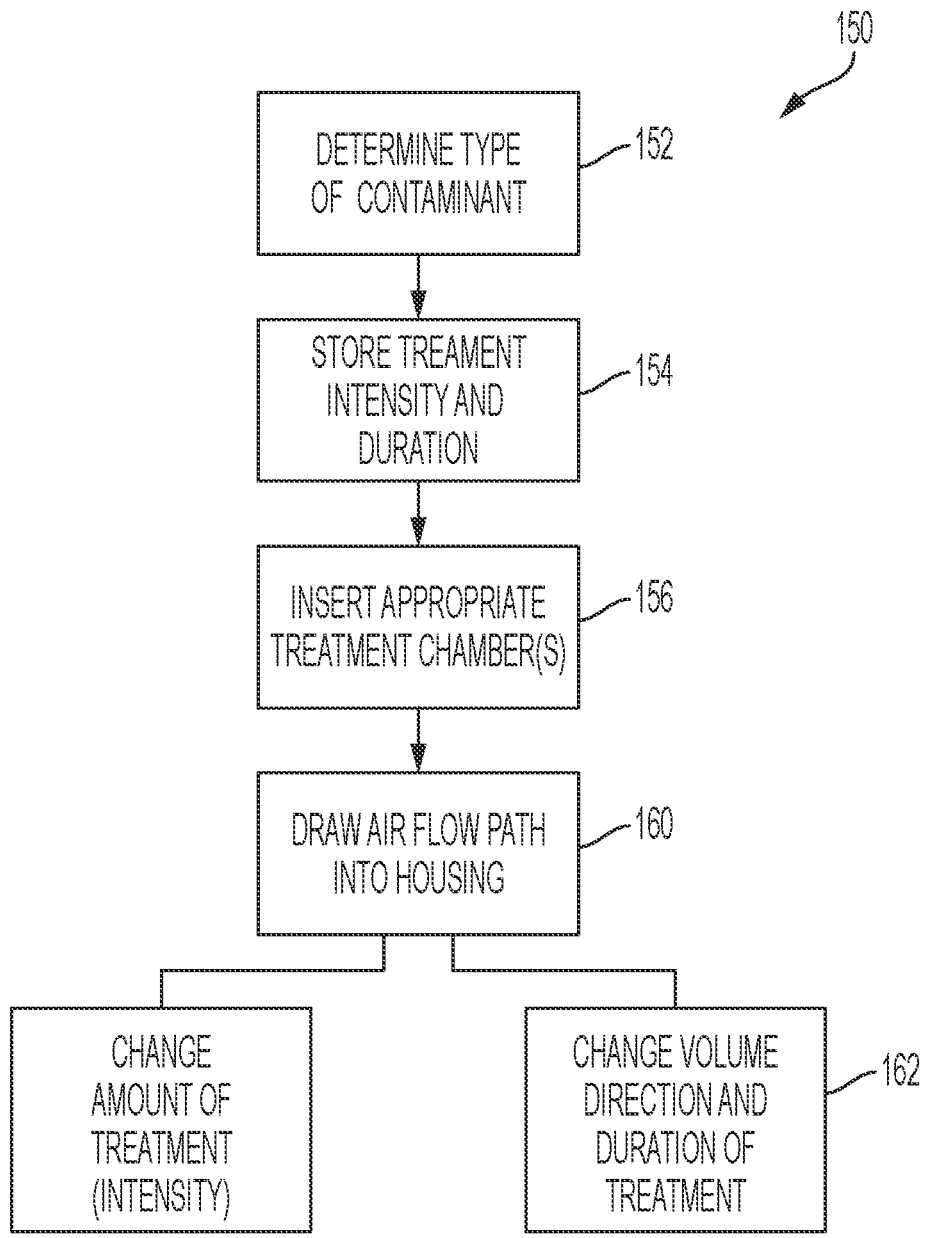
FIG. 6 is a flow diagram of a method for customizing the apparatus to a particular contaminate needing sterilization, and for sterilizing the air containing that contaminate in accordance with various examples.

FIG. 6 is a flow diagram 150 is various operations performed in customizing the apparatus for a particular treatment. The method begins by determining the type of contaminant present and to be treated or sterilized 152. Then, the treatment recipe is downloaded and stored in memory 154. The treatment recipe may include the intensity of the UV lamp output or the duration at which air is must be exposed in the UV chamber to the UV lamp, for example. Next, the appropriate number and arrangement of treatment chambers from a pre-manufactured set of self-contained chamber is inserted into the housing depending on the contaminant being treated, as shown in block 156.

Once the apparatus has been customized with the appropriate treatment recipe, and with the appropriate number of chambers and chamber arrangement, air is then drawn into the housing 160 via the fan. The air flow originated from the fan can be programmably and independently changed in each chamber by changing the volume, direction and duration of treatment 162. Moreover, the intensity output from the treatment devices (e.g., UV lamp, heater, cooler and catalyst element) can be programmably and independently changed in each chamber 164.

In the foregoing discussion and in the claims, the terms "including" and "comprising" are used in an open-ended fashion, and thus should be interpreted to mean "including, but not limited to . . . ." Also, the term "couple" or "couples" is intended to mean either an indirect or direct connection. Thus, if a first device couples to a second device, that connection may be through a direct connection or through an indirect connection via other devices and connections. Similarly, a device that is coupled between a first component or location and a second component or location may be through a direct connection or through an indirect connection via other devices and connections. An element or feature that is "configured to" perform a task or function may be configured (e.g., programmed or structurally designed) at a time of manufacturing by a manufacturer to perform the function and/or may be configurable (or re-configurable) by a user after manufacturing to perform the function and/or other additional or alternative functions. The configuring may be through firmware and/or software programming of the device, through a construction and/or layout of hardware components and interconnections of the device, or a combination thereof. Unless otherwise stated, "about," "approximately," or "substantially" preceding a value means +/−10 percent of the stated value. The above discussion is meant to be illustrative of the principles and various embodiments of the present disclosure. Numerous variations and modifications will become apparent to those skilled in the art once the above disclosure is fully appreciated. It is intended that the following claims be interpreted to embrace all such variations and modifications.

What is claimed is:

1. A method for capturing and sterilizing contaminated air, comprising:
   inserting at least one self-contained treatment chamber comprising a UV chamber, a temperature chamber or an ozone converter chamber, or a combination thereof, into a housing;
   drawing an air flow path of contaminated air into the housing and through the at least one treatment chamber;
   programmably and independently changing the volume, direction and duration of the air flow path through the at least one treatment chamber, wherein programmably and independently changing the volume, direction and duration of the air flow path comprises moving a baffle configured within each of the UV chamber and the temperature chamber to independently change the volume and direction of the air flow path within the UV chamber and the temperature chamber; and
   programmably and independently changing the amount of treatment of the contaminated air within the air flow path through the at least one treatment chamber.

2. The method of claim 1, wherein inserting comprises electrically connecting a UV lamp and UV sensor contained entirely within the UV chamber to a processor and memory containing instructions for programmably changing an amount of output from the UV lamp based on UV radiation sensed by the UV sensor.

3. The method of claim 1, wherein inserting comprises electrically connecting a heater and a temperature sensor contained entirely within the temperature chamber to a processor and memory containing instructions for programmably changing an amount of output from the heater based on temperature sensed by the temperature sensor.

4. The method of claim 1, wherein programmably and independently changing the amount of treatment of the contaminated air within the air flow path comprising moving a damper configured within each of the UV chamber and the temperature chamber to independently re-direct air flow back within the UV chamber and the temperature chamber to maintain the re-directed air flow within the UV chamber and the temperature chambers at independent durations.

5. The method of claim 1, further comprises removing at least one self-contained treatment chamber after said inserting to reconfigure the number or arrangement of self-contained treatment chambers within the housing.

6. The method of claim 1, wherein inserting comprises arranging within the housing in different slots the temperature chamber and the UV chamber.

7. The method of claim 1, wherein inserting comprises arranging within the housing in different slots the temperature chamber downstream of the airflow path within the UV chamber.

8. The method of claim 1, wherein inserting comprises arranging within the housing in different slots the ozone converter chamber and the temperature chamber.

9. The method of claim 1, wherein inserting comprises arranging within the housing in different slots the ozone converter chamber downstream of the airflow path within the temperature chamber.

10. The method of claim 1, wherein inserting comprises electrically connecting a cooler and a temperature sensor contained entirely within the temperature chamber to a processor and memory containing instructions for programmably changing an amount of output from the cooler based on temperature sensed by the temperature sensor.

11. The method of claim 1, wherein programmably and independently changing the amount of treatment of the contaminated air comprises changing the amount of treatment from a corresponding treatment chamber to a desired treatment amount stored in memory.

12. The method of claim 11, wherein changing the amount of treatment to a desired treatment amount comprises changing based on previously stored treatment profile data unique to a particular contaminate targeted for elimination.

13. The method of claim 1, wherein inserting comprises:
   determining the contaminate targeted for elimination;
   moving the housing into position within a room and removing panels for gaining access to electrical connectors and slide-in grooves or ridges on the inside of the housing; and
   sliding within the grooves or ridges at least one self-contained treatment chamber in a customized order at proper locations electrically coupled to the electrical connectors for removing the targeted contaminate.

14. The method of claim 1, wherein programmably and independently changing the volume, direction and duration of the air flow path comprises wireless network communicating an instruction from a transmitter.

* * * * *